United States Patent
Geerlings et al.

(10) Patent No.: US 6,977,237 B2
(45) Date of Patent: Dec. 20, 2005

(54) CATALYST AND PROCESS FOR THE PREPARATION OF HYDROCARBONS

(75) Inventors: Jacobus Johannes Cornelis Geerlings, Amsterdam (NL); Hans Michiel Huisman, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/851,596

(22) Filed: May 21, 2004

(65) Prior Publication Data

US 2004/0214905 A1   Oct. 28, 2004

Related U.S. Application Data

(62) Division of application No. 10/332,019, filed as application No. PCT/EP01/07448 on Jan. 3, 2003, now Pat. No. 6,759,440.

(30) Foreign Application Priority Data

Jul. 3, 2000   (EP) .................................. 00305613

(51) Int. Cl.⁷ .......................... B01J 23/32; B01J 23/40; B01J 23/00
(52) U.S. Cl. ...................... 502/326; 502/324; 502/350
(58) Field of Search ............................... 502/324, 326, 502/350, 241, 242, 260

(56) References Cited

U.S. PATENT DOCUMENTS

| 3,956,185 | A | * | 5/1976 | Yagi et al. .................... 502/241 |
| 4,077,913 | A | * | 3/1978 | Acres et al. ................. 502/302 |
| 4,701,434 | A | * | 10/1987 | Koll ............................ 502/230 |
| 5,958,985 | A |   | 9/1999 | Geerlings et al. ........... 518/700 |
| 6,121,187 | A | * | 9/2000 | Maier ......................... 502/232 |
| 6,130,184 | A | * | 10/2000 | Geerlings et al. ........... 502/350 |
| 6,333,294 | B1 | * | 12/2001 | Chao et al. ................. 502/325 |

FOREIGN PATENT DOCUMENTS

WO   WO 96/01146   1/1996

OTHER PUBLICATIONS

Patent Application No. 2003102895 (PCT/EP01/07448) in the Russian Federation (translation and response).

* cited by examiner

*Primary Examiner*—Cam N. Nguyen

(57) ABSTRACT

The invention provides a process for the production of mainly $C_5+$ hydrocarbons, which process involves contacting carbon monoxide and hydrogen at a temperature in the range of from about 180° C. to about 270° C. and elevated pressure in the presence of a catalyst composition having cobalt, manganese and at least one of rhenium and/or ruthenium on a titania carrier. The invention also relates to a catalyst composition having cobalt, manganese and rhenium on a titania carrier.

4 Claims, No Drawings

CATALYST AND PROCESS FOR THE PREPARATION OF HYDROCARBONS

This is a division of application Ser. No. 10/332,019 filed Jan. 3, 2003 now U.S. Pat. No. 6,759,440, which is a 371 of PCT/EP01/07448 filed Jun. 29, 2001, the entire disclosure of which is hereby incorporated by reference.

FIELD OF THE INVENTION

The present invention relates to a catalyst and process for the preparation of hydrocarbons from synthesis gas.

BACKGROUND OF THE INVENTION

The preparation of hydrocarbons from a gaseous mixture comprising carbon monoxide and hydrogen (synthesis gas) by contacting the mixture with a catalyst at elevated temperature and pressure is well known in the art and is commonly referred to as Fischer-Tropsch synthesis.

Catalysts that may be suitably used in a Fischer-Tropsch synthesis process typically contain one or more catalytically active metals from Groups 8 to 10 of the Periodic Table of the Elements. In particular, iron, nickel, cobalt and ruthenium are well known catalytically active metals for such catalyst and may be optionally combined with one or more metal oxides and/or metals as promoters. Cobalt has been found to be the most suitable for catalysing a process in which synthesis gas is converted to primarily paraffinic hydrocarbons containing 5 or more carbon atoms. In other words, the $C_5+$ selectivity of the catalyst is high.

Similar catalyst compositions are also known in other fields including JP-A-404122454 which describes an exhaust gas purification catalyst comprising an active platinum group element such as ruthenium, rubidium, palladium and platinum or a metal oxide such as chromium, manganese, cobalt and nickel on an alumina, silica, titania, silica-titania or alumina-titania carrier. Catalysts of the invention are fitted in an exhaust gas purification catalytic converter and may be used in controlling emissions from gasoline engines.

U.S. Pat. No. 5,134,109 provides a catalyst for the steam reforming of hydrocarbons, which comprises at least one metal from rhodium and ruthenium and at least one metal from cobalt and manganese deposited on a carrier which is preferably zirconia or stabilised zirconia.

JP-A-60064631 discloses a catalyst comprising an iron group metal such as cobalt and iron, a platinum group metal such as ruthenium, rhodium, palladium, platinum and iridium, and manganese oxide, supported on a carrier comprising titanium oxide. JP-A-60064631 further discloses a method for the production of high calorie gas containing hydrocarbons of 1–4 carbons for use as fuels, from low calorie gas containing a mixture of hydrogen, carbon monoxide and optionally carbon dioxide.

JP-A-60064631 is primarily concerned with a method for the production of methane and $C_{2-4}$ hydrocarbons and does not concern itself in any way with increasing % $C_5+$ selectivity during the conversion of low calorie gas. Indeed, it can seen from Example 2 therein, which is the only example of conversion of a simple $CO/H_2$ mixture, that the treatment of a mixture of 3 parts $H_2$ and 1 part CO in the presence of a catalyst composition comprising 10% Co, 6% $Mn_2O_3$ and 2% Ru on a titanium carrier, results in 74.6% $CH_4$, 7.3% $C_2H_6$, 5.5% $C_3H_8$, 2.6% $C_4H_{10}$ and 10.0% $CO_2$ (by % volume), i.e. the presence of $C_5+$ hydrocarbons was not detected. This conversion was effected at 320° C., and although the broadest temperature range disclosed for the process is 150 to 400° C., it is stated that the preferred range is 260 to 350° C.

Although, U.S. Pat. No. 4,568,663 describes a rhenium-promoted cobalt catalyst on an inorganic oxide support which is preferably titania, which catalyst may be employed in production of hydrocarbons by both FT synthesis and the conversion of methanol, as being highly active, this disclosure is discussed in column 2, lines 19 to 35, of U.S. Pat. No. 4,857,559, and contrasted with the corresponding alumina-supported catalyst, which has significantly higher activity.

Much research effort has been directed to finding catalysts having a higher $C_5+$ selectivity than known catalysts at the same or higher activity.

U.S. Pat. No. 4,857,559 concerns the addition of rhenium to cobalt on a number of common supports including alumina, silica, titania, chromia, magnesia and zirconia and a process for the FT synthesis of hydrocarbons using said catalyst. However, it is recognised therein (e.g. column 4, lines 54 to 59 and column 15, lines 51–55) that whilst supports other than alumina may be used, such supports produce catalysts with much lower activities. It is found in U.S. Pat. No. 4,857,559 that the hydrocarbon yield obtained by the addition of rhenium to alumina-supported cobalt catalyst is greater than the corresponding titania-supported catalyst. In particular, the FT conversion of synthesis gas into hydrocarbons show lower % $CH_4$ selectivity, higher % CO conversion and higher $C_2+$ selectivity for rhenium-promoted cobalt catalysts on alumina, than for similar catalysts on titania (Table 1).

TABLE 1

| Example No. | % Co | % Re | Support | % CO Conversion | % Selectivity $C_2+$ | $CH_4$ | $CO_2$ |
|---|---|---|---|---|---|---|---|
| 8  | 12 | 1 | $Al_2O_3$ | 33 | 87.7 | 11.4 | 0.9 |
| 30 | 12 | — | $TiO_2$*  | 11 | 87.6 | 11.8 | 0.6 |
| 31 | 12 | 1 | $TiO_2$*  | 17 | 86.5 | 12.8 | 0.7 |
| 32 | 12 | — | $TiO_2$** | 11 | 87.6 | 11.7 | 0.7 |
| 33 | 12 | 1 | $TiO_2$** | 17 | 85.8 | 13.5 | 0.7 |

*support calcined at 500° C.
**support calcined at 600° C.

Based on the above disclosure, the person skilled in the art would clearly deduce that $TiO_2$ should be avoided as catalyst carrier for rhenium/cobalt combinations in favour of $Al_2O_3$.

Fischer-Tropsch synthesis of hydrocarbons produces a number of by-products such as carbon dioxide, water and gaseous $C_{1-4}$ hydrocarbons.

As well as improving % CO conversion, it is of prime importance to be able to adjust the product slate in any given Fischer-Tropsch reaction, to satisfy individual requirements such as increased % $C_5+$ selectivity and reduced $CH_4$ and $CO_2$ production.

It is highly desirable to reduce the amount of carbon dioxide evolved during Fischer-Tropsch synthesis of hydrocarbons for both economic and environmental reasons. It is particularly desirable to restrict the level of carbon dioxide by-product in such process to less than 2% v/v, preferably less than 1% v/v.

Of prime importance is that any methodologies employed for a reduction in carbon dioxide selectivity in Fischer-Tropsch synthesis, do not cause a concomitant reduction in $C_5+$ hydrocarbon selectivity.

It can be seen from Table 1, that whilst the addition rhenium to a cobalt catalyst on titania gives a modest increase in activity from 11% carbon monoxide conversion to 17% carbon monoxide conversion, the $C_2+$ selectivity is reduced and the $CO_2$ selectivity is equal or increased compared to the corresponding unpromoted catalyst.

WO-A-97/00231 relates to a catalyst comprising cobalt and manganese and/or vanadium supported on a carrier wherein the cobalt:(manganese+vanadium) atomic ratio is at least 12:1.

Said catalyst exhibits higher $C_5+$ selectivity and higher activity when used in the Fischer-Tropsch synthesis of hydrocarbons, compared to catalysts containing cobalt only, or containing a relatively higher amount of manganese and/or vanadium. Preferred carriers include titania, zirconia and mixtures thereof.

It is highly desirable not only to increase further the $C_5+$ selectivity of such cobalt manganese catalysts, but also to reduce their carbon dioxide selectivity.

It has now been surprisingly found that the addition of small quantities of rhenium and/or ruthenium to cobalt-manganese catalyst compositions can not only cause reductions in carbon dioxide selectivity, but can also have dramatic effects on the product slate obtained from FT hydrocarbon synthesis reactions.

SUMMARY OF THE INVENTION

Accordingly, the present invention provides a process for the production of mainly $C_5+$ hydrocarbons comprising contacting carbon monoxide and hydrogen at a temperature in the range of from about 180° C. to about 270° C. and elevated pressure in the presence of a catalyst composition comprising cobalt, manganese and at least one of rhenium and/or ruthenium on a titania carrier.

DETAILED DESCRIPTION OF THE INVENTION

According to another aspect, the present invention provides a catalyst composition comprising cobalt, manganese and rhenium on a titania carrier.

By "mainly" in the present invention is meant an amount greater than about 80 wt. % based on the paraffinic hydrocarbon and carbon dioxide distribution.

By "product slate" in the present invention is meant the overall product distribution resulting from Fischer-Tropsch synthesis of hydrocarbons, i.e. the relative amounts of $C_{1-4}$ hydrocarbons, $C_5+$ hydrocarbons, water and carbon dioxide present in the product mixture.

The rutile:anatase weight ratio in the titania carrier is not limited in the present invention, however, said ratio may conveniently be less than about 2:3, as determined by ASTM D 3720-78.

The titania carrier may be prepared by any method known in the art, however it is particularly preferred that the titania carrier is prepared in the absence of sulphur-containing compounds. An example of such a preparation method involves flame hydrolysis of titanium tetrachloride. It will be appreciated that the titania powder derived from such a preparation method may not be of the desired size and shape. Thus, usually a shaping step is required to prepare the carrier. Shaping techniques are well known to those skilled in the art and include pelletising, extrusion, spray-drying, and hot oil dropping methods.

Titania is available commercially and is well-known as a material for use in the preparation of catalysts or catalyst precursors.

As an alternative or in addition to titania, the mixture may comprise a titania precursor. Titania may be prepared by heating titanium hydroxide. As the heating progresses, titanium hydroxide is converted via a number of intermediate forms and the successive loss of a number of water molecules into titania. For the purpose of this specification, the term "titania precursor" is to be taken as a reference to titanium hydroxide or any of the aforementioned intermediate forms.

Catalysts that may be used in the process of present invention preferably contain from about 5 wt. % to about 30 wt. % of Co based on the total weight of the catalyst composition, more preferably from about 10 wt. % to about 25 wt. % of Co based on the total weight of the catalyst composition, and most preferably about 15 wt. % to about 25 wt. % of Co based on the total weight of the catalyst composition.

Catalysts that may be used in the process of present invention preferably contain from 0.01 wt. % to about 5 wt. % of Mn based on the total weight of the catalyst composition, more preferably from about 0.01 wt. % to about 1.5 wt. % of Mn based on the total weight of the catalyst composition.

Catalysts that may be used in the process of present invention preferably contain from about 0.01 wt. % to about 5 wt. % each of rhenium and/or ruthenium based on the total weight of the catalyst composition, more preferably from about 0.01 wt. % to about 1 wt. % each of rhenium and/or ruthenium based on the total weight of the catalyst composition, and most preferably from about 0.01 wt. % to about 0.5 wt. % each of rhenium and/or ruthenium based on the total weight of the catalyst composition.

Catalysts that may be used in the process of the present invention may further comprise up to about 20 wt. % of a binder material such as alumina or silica based on the total weight of the catalyst composition, preferably up to about 10 wt. % of a binder material such as alumina or silica based on the total weight of the catalyst composition.

The pore size and volume of the catalyst composition prior to activation are not limited in the present invention. The pore volume may conveniently be in the range of from about 0.1 cm$^3$/g to about 0.8 cm$^3$/g, preferably in the range of from about 0.15 cm$^3$/g to about 0.7 cm$^3$/g, more preferably in the range of from about 0.2 cm$^3$/g to about 0.5 cm$^3$/g.

The catalyst of the present invention may be prepared by methods known to those skilled in the art, such as by precipitating the catalytically active compounds or precursors onto the carrier; spray-coating, kneading and/or impregnating the catalytically active compounds or precursors onto the carrier; and/or extruding one or more catalytically active compounds or precursors together with carrier material to prepare catalyst extrudates.

It will be appreciated by those skilled in the art that the most preferred method of preparation may vary, depending e.g. on the desired size of the catalyst particles. It belongs to the skill of the skilled person to select the most suitable method for a given set of circumstances and requirements.

Extrusion may be effected using any conventional, commercially available extruder. In particular, a screw-type extruding machine may be used to force the mixture through the orifices in a suitable dieplate to yield extrudates of the desired form. The strands formed upon extrusion may be cut to the desired length.

After extrusion, the extrudates are dried. Drying may be effected at an elevated temperature, preferably up to about 500° C., more preferably up to about 300° C. The period for drying is typically up to 5 hours, more preferably from about 15 minutes to about 3 hours.

The extruded and dried catalyst composition may be calcined. Calcination is effected at elevated temperature, typically in the range of from about 200° C. to about 900° C., preferably at a temperature in the range of from about 400° C. to about 750° C., more preferably in the range of from about 500° C. to about 650° C. The duration of calcination treatment is conveniently from about 5 minutes to several hours, preferably from about 15 minutes to about 4 hours.

Conveniently, the calcination treatment is carried out in an oxygen-containing atmosphere, preferably air. It will be appreciated that, optionally, the drying step and the calcining step may be combined.

A preferred method of preparing the catalyst according to the present invention is by impregnating the catalytically active compounds or precursors onto a carrier. Thus, typically the carrier is impregnated with a solution of a cobalt compound, a solution of a rhenium and/or ruthenium compound and a solution of a manganese compound. Preferably, the carrier is impregnated simultaneously with the respective metal compounds. Thus, according to a preferred embodiment, the process for preparing the catalyst for use in the process of the present invention comprises co-impregnating the carrier with a solution of a cobalt compound, a solution of a rhenium and/or ruthenium compound and a solution of a manganese compound.

A further preferred method of preparing the catalyst according to the present invention is by mixing some of the catalytically active compounds or precursors with the carrier, followed by extruding the resulting mixture, followed by drying and calcining the extrudate, followed by impregnating with further catalytically active compounds or precursors to prepare catalyst extrudates for use in the process of the present invention.

Thus, typically the carrier is mixed with a cobalt compound and a manganese compound and water followed by extrusion of the resulting mixture, and after drying and calcining, followed by impregnation with a solution of a rhenium and/or ruthenium compound to prepare catalyst extrudates for use in the process of the present invention. Preferably, the carrier is mixed simultaneously with the cobalt and manganese compounds.

Thus, according to a preferred embodiment, the process for preparing the catalyst for use in the process of the present invention comprises co-extruding the carrier with a cobalt compound and a manganese compound, followed by impregnating the extrudate with a solution of a rhenium and/or ruthenium compound.

Examples of suitable cobalt compounds that may be used in the preparation of said catalyst include one or more of cobalt hydroxide, cobalt oxide, cobalt carbonyl, halides such as cobalt chloride (hexahydrate or anhydrous), inorganic acid salts such as cobalt sulphate, cobalt nitrate or cobalt carbonate, and organic acid salts such as cobalt acetate and cobalt formate. Preferred cobalt compounds include cobalt hydroxide, cobalt carbonate and cobalt nitrate.

Examples of suitable rhenium compounds that may be used in the preparation of said catalyst include one or more of rhenium oxide, rhenium chloride, rhenium carbonyl, ammonium perrhenate and perrhenic acid. The preferred rhenium compound is ammonium perrhenate.

Examples of suitable ruthenium compounds that may be used in the preparation of said catalyst include one or more of a ruthenium halide such as ruthenium chloride or ruthenium iodide, a ruthenic halide or salt thereof, for example ruthenic chloride, ammonium ruthenic chloride, sodium ruthenic chloride, potassium ruthenic chloride, a ruthenium oxide such as ruthenium di or tetraoxide, a ruthenic acid salt such as potassium ruthenate or sodium ruthenate, an organic ruthenium compound such as ruthenium carbonyl, ruthenium nitrosyl nitrate. The preferred ruthenium compound is ruthenium nitrosyl nitrate.

Examples of suitable manganese salts that may be used in the preparation of said catalyst include one or more of manganese hydroxide, manganese oxide, halides such as manganese chloride, inorganic acid salts such as manganese sulphate, manganese nitrate or manganese carbonate, and organic acid salts such as manganese acetate and manganese formate. Preferred manganese compounds include manganese hydroxide, manganese nitrate and manganese acetate.

The impregnation treatment is typically followed by drying and, optionally, calcining. Drying is typically carried out at a temperature in the range of from about 50° C. to about 300° C. for up to about 24 hours, preferably from about 1 to about 4 hours.

Calcination is typically carried out at a temperature in the range of from about 200° C. to about 900° C., preferably, in the range of from about 250° C. to about 700° C. The duration of the calcination treatment is typically from about 0.5 to about 24 hours, preferably from about 1 to about 4 hours. Suitably, the calcination treatment will normally be higher than the average temperature during the drying treatment.

When in use, the catalyst for the process of the present invention may contain at least part of the cobalt in its metallic form.

Therefore, it is normally advantageous to activate the catalyst prior to use by a reduction treatment, in the presence of hydrogen at elevated temperature. Typically, the reduction treatment involves treating the catalyst at a temperature in the range of from about 100° C. to about 450° C. for 1 to 48 hours at elevated pressure, typically from about 0.1 MPa to about 20.0 MPa (1 to 200 bar abs.). Pure hydrogen may be used in the reduction treatment, but it is usually preferred to apply a mixture of hydrogen and an inert gas, such as nitrogen. The relative amount of hydrogen present in the mixture may range from between 0% to about 100% by volume.

According to one preferred embodiment, the catalyst is brought to the desired temperature and pressure level in a nitrogen gas atmosphere and subsequently, the catalyst is contacted with a gas mixture containing only a small amount of hydrogen gas, the rest being nitrogen gas. During the reduction treatment, the relative amount of hydrogen gas in the gas mixture is gradually increased up to about 50% or even about 100% by volume.

If possible, it is preferred to activate the catalyst in situ i.e. inside the reactor. WO-A-97/17137 describes an in situ catalyst activation process which comprises contacting the catalyst in the presence of hydrocarbon liquid with a hydrogen-containing gas at a hydrogen partial pressure of at least about 1.5 MPa (15 bar abs.), preferably at least about 2.0 MPa (20 bar abs.), more preferably at least about 3.0 MPa (30 bar abs.). Typically, in this process the hydrogen partial pressure is at most about 20 MPa (200 bar abs.).

It is advantageous to rejuvenate spent catalyst, i.e. catalyst that has lost at least part of the initial activity of an activated fresh catalyst, by subjecting it to a hydrogen strip or an ROR treatment. Conveniently, the ROR treatment involves the steps, in sequence, of reduction with a hydrogen-containing gas, oxidation with an oxygen-containing gas, and reduction with a hydrogen-containing gas.

The process of the present invention is preferably carried out at a temperature in the range of from about 200° C. to about 250° C. The pressure is typically in the range of from about 0.5 MPa to about 15.0 MPa (5 to 150 bar abs.), preferably in the range of from about 1.0 Mpa to about 8.0 MPa (10 to 80 bar abs.), in particular from about 1.0 Mpa to about 6.0 MPa (10 to 60 bar abs.).

Hydrogen and carbon monoxide (synthesis gas) may be conveniently fed to the process at a molar ratio in the range of from about 1 to about 2.5.

The gas hourly space velocity (GHSV) of the synthesis gas in the process of the present invention may vary within wide ranges and is typically in the range of from about 400 to about 10000 Nl $l^{-1}h^{-1}$, for example from about 400 to about 4000 Nl $l^{-1}h^{-1}$. The term GHSV is well known in the art, and relates to the volume of synthesis gas in Nl, i.e. liters at standard temperature and pressure (STP) conditions (0° C. and 1 bar abs.), which is contacted in one hour with one liter of catalyst particles, i.e. excluding interparticular void spaces for slurry reactions. In the case of a fixed catalyst bed, the GHSV may also be expressed as per liter of catalyst bed, i.e. including interparticular void space.

The process of the present invention for the preparation of hydrocarbons may be conducted using a variety of reactor types and reaction regimes, for example a fixed bed regime, a slurry phase regime or an ebullating bed regime. It will be appreciated that the size of the catalyst particles may vary depending on the reaction regime they are intended for. It belongs to the skill of the skilled person to select the most appropriate catalyst particle size for a given reaction regime.

Further, it will be understood that the skilled person is capable of selecting the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity is chosen in the range of from about 500 to about 2500 Nl $l^{-1}h^{-1}$. If it is desired to operate the hydrocarbon synthesis process with a slurry phase regime, preferably the gas hourly space velocity is chosen in the range of from about 1500 to about 7500 Nl $l^{-1}h^{-1}$.

The present invention is illustrated by the following Examples, which should not be regarded as limiting the scope of the invention in any way.

EXAMPLES

Example 1 (Comparative)

A mixture was prepared containing 112.5 g of commercially available titania powder (p25 ex. Degussa), 49.5 g of commercially available Co(OH)$_2$ powder, 8.2 g Mn(Ac)$_2$.4H$_2$O (wherein "Ac" represents acetate) and 45 g water. The mixture was kneaded for 30 minutes. The mixture was shaped by means of an extruder.

The extrudates were dried for 2 hours at 120° C. and subsequently calcined for 2 hours at 500° C.

The catalyst (I) thus produced, contained 22% by weight of cobalt compounds, expressed as cobalt metal, and 1.2% by weight of manganese compounds, expressed as manganese metal, based on the total weight of the catalyst composition.

Example 2

A portion of catalyst (I) was impregnated with an aqueous solution of ammonium perrhenate (NH$_4$ReO$_4$).

The extrudates were dried for 2 hours at 120° C. and calcined for 2 hours at 500° C.

The catalyst (II) thus produced, contained 22% by weight of cobalt compounds, expressed as cobalt metal, 1.2% by weight of manganese compounds, expressed as manganese metal, and 0.18% by weight of rhenium compounds, expressed as rhenium metal (9.7×10$^{-6}$ mol Re/gram catalyst), based on the total weight of the catalyst composition.

Example 3

A portion of catalyst (I) was impregnated with an aqueous solution of ruthenium nitrosyl nitrate (Ru(NO)(NO$_3$)$_x$(OH)$_y$, x+y=3).

The extrudates were dried for 2 hours at 120° C. and calcined for 2 hours at 500° C.

The catalyst (III) thus produced, contained 22% by weight of cobalt compounds, expressed as cobalt metal, 1.2% by weight of manganese compounds, expressed as manganese metal, and 0.10% by weight of ruthenium compounds, expressed as ruthenium metal (9.9×10$^{-6}$ mol Ru/gram catalyst).

Example 4

Catalyst testing was performed according to the method described in WO-A-97/00231. Catalysts I, II, and III were tested in a process for the preparation of hydrocarbons. Microflow reactors A, B, and C, containing 10 ml of catalysts I, II, and III respectively, in the form of a fixed bed of catalyst particles were heated to a temperature of 260° C., and pressurised with a continuous flow of nitrogen gas to a pressure of 0.2 MPa (2 bar abs.). The catalysts were reduced in situ for 24 hours with a mixture of nitrogen and hydrogen gas. During reduction, the relative amount of hydrogen in the mixture was gradually increased from 0% to 100%. The water concentration in the off-gas was kept below 3000 ppmv.

Following reduction, the pressure was increased to 2.6 MPa (26 bar abs.). The reaction was carried out with a mixture of hydrogen and carbon monoxide at a H$_2$/CO ratio of 1.1:1. The GHSV amounted to 800 Nl $l^{-1}h^{-1}$. The reaction temperature is expressed as the weighted average bed temperature (WABT) in ° C. The space time yield (STY), expressed as grammes hydrocarbon product per liter catalyst particles (including the voids between the particles) per hour, the C$_5$+ selectivity, expressed as a weight percentage of the total hydrocarbon product, and the CO$_2$ selectivity, expressed as a molar percentage of the CO converted, were determined for each experiment after 50 hours of operation. The results are set out in Table I.

TABLE I

| Catalyst | I | II | III |
|---|---|---|---|
| WABT (° C.) | 209 | 202 | 206 |
| STY (g $l_{cat}^{-1}h^{-1}$) | 100 | 100 | 100 |
| C$_5$+ selectivity (%) | 92 | 95 | 94 |
| CO$_2$ selectivity (%) | 1.2 | 1.0 | 0.8 |

It will be appreciated that, in addition to the reduction in CO$_2$ selectivity, the activity and C$_5$+ selectivity of both catalysts II and III, according to the invention, is much better than that of catalyst I.

We claim:

1. A catalyst composition comprising cobalt, manganese and rhenium on a titania carrier, wherein the catalyst contains from about 5 wt. % to about 30 wt. % of Co, based on the total weight of the catalyst composition, and from about 0.01 wt. % to about 5 wt. % of Re based on the total weight of the catalyst composition and wherein the pore volume of the catalyst composition is in the range of from about 0.1 cm$^3$/g to about 0.8 cm$^3$/g.

2. The catalyst composition of claim 1, wherein the catalyst contains from about 0.01 wt. % to about 5 wt. % of Mn based on the total weight of the catalyst composition.

3. An activated catalyst for the production of hydrocarbons by reduction with hydrogen at an elevated temperature wherein the catalyst comprises cobalt, manganese and rhenium on a titania carrier, wherein the catalyst contains from about 5 wt. % to about 30 wt. % of Co, based on the total weight of the catalyst composition, and from about 0.01 wt. % to about 5 wt. % of Re based on the total weight of the catalyst composition and wherein the pore volume of the catalyst composition prior to activation is in the range of from about 0.1 cm$^3$/g to about 0.8 cm$^3$/g.

4. A process for the production of a catalyst composition comprising cobalt, manganese and rhenium on a titania carrier, wherein the catalyst contains from about 5 wt. % to about 30 wt. % of Co, based on the total weight of the catalyst composition, and from about 0.01 wt. % to about 5 wt. % of Re based on the total weight of the catalyst composition and wherein the pore volume of the catalyst composition is in the range of from about 0.1 cm$^3$/g to about 0.8 cm$^3$/g which process comprises extruding the titania carrier with a cobalt compound and a manganese compound, followed by drying and, optionally, calcining, and then impregnating with a solution of a rhenium salt.

* * * * *